United States Patent
Tao et al.

(10) Patent No.: US 10,493,378 B2
(45) Date of Patent: Dec. 3, 2019

(54) METHOD OF FORMING MICRO-PIPES ON A SUBSTRATE AND A STRUCTURE FORMED THEREOF

(71) Applicant: IMEC VZW, Leuven (BE)

(72) Inventors: Zheng Tao, Heverlee (BE); Boon Teik Chan, Leuven (BE); XiuMei Xu, Bertem (BE); Khashayar Babaei Gavan, Oud-Heverlee (BE); Efrain Altamirano Sanchez, Kessel-Lo (BE)

(73) Assignee: IMEC VZW, Leuven (BE)

( * ) Notice: Subject to any disclaimer, the term of this patent is extended or adjusted under 35 U.S.C. 154(b) by 0 days.

(21) Appl. No.: 15/674,438

(22) Filed: Aug. 10, 2017

(65) Prior Publication Data

US 2018/0043283 A1     Feb. 15, 2018

(30) Foreign Application Priority Data

Aug. 11, 2016    (EP) .................................... 16183687

(51) Int. Cl.
*B01D 15/10*    (2006.01)
*B01D 63/14*    (2006.01)
(Continued)

(52) U.S. Cl.
CPC ......... *B01D 15/10* (2013.01); *B01D 53/0407* (2013.01); *B01D 63/14* (2013.01);
(Continued)

(58) Field of Classification Search
CPC .... B01D 15/10; B01D 53/0407; B01D 69/06; B01D 69/10; B01D 69/105; B01D 69/12; B01D 69/125; B01D 71/02; B01D 71/022; B01D 71/024; B01D 71/025; B01D 2325/06; B01D 2325/12; B01D 63/02; B01D 63/028; B01D 63/029; B01D 63/04;
(Continued)

(56) References Cited

U.S. PATENT DOCUMENTS 5,660,728 A * 8/1997 Saaski ............... A61M 5/16881
                                                 210/137
5,753,014 A * 5/1998 Van Rijn ............ B01D 39/1692
                                                 55/524

(Continued)

OTHER PUBLICATIONS

European Search Report, European Patent Application No. 16183687.9, dated Feb. 3, 2017, 7 pages.

*Primary Examiner* — Joseph W Drodge
(74) *Attorney, Agent, or Firm* — McDonnell Boehnen Hulbert & Berghoff LLP (57) ABSTRACT

A method for producing a structure including, on a main surface of a substrate, at least one elongated cavity having openings at opposing ends. The method includes providing a substrate having a main surface. On the main surface, a first pair of features are formed that protrude perpendicularly from the main surface. The features have elongated sidewalls and a top surface, are parallel to one another, are separated by a gap having a width s1 and a bottom area, and have a width w1 and a height h1. At least the main surface of the substrate and the first pair of features are brought in contact with a liquid, suitable for making a contact angle of less than 90° with the material of the elongated sidewalls and subsequently the substrate is dried.

8 Claims, 6 Drawing Sheets

(51) Int. Cl.
    *B01L 3/00* (2006.01)
    *C12M 1/12* (2006.01)
    *B81C 1/00* (2006.01)
    *C12M 1/26* (2006.01)
    *B01D 53/04* (2006.01)

(52) U.S. Cl.
    CPC .... *B01L 3/502753* (2013.01); *B81C 1/00119* (2013.01); *C12M 1/123* (2013.01); *C12M 33/14* (2013.01); *B01L 2300/0896* (2013.01); *B81B 2201/058* (2013.01); *B81B 2201/10* (2013.01); *B81B 2203/0315* (2013.01); *B81B 2203/0338* (2013.01); *B81B 2203/0346* (2013.01); *B81B 2203/0384* (2013.01)

(58) Field of Classification Search
    CPC ... B01D 63/067; B01D 63/14; B81C 1/00119; B81B 2203/0384; B81B 2203/0346; B81B 2203/0338; B81B 2203/0315; B81B 2201/058; B81B 2201/10; B81B 7/00; B81B 7/0006; C12M 1/12; C12M 1/123; C12M 1/126; C12M 33/14; C12M 47/10; C12M 47/12; B01L 3/502; B01L 3/5025; B01L 3/50255; B01L 3/5027; B01L 3/502707; B01L 3/502753; B01L 2300/0861; B01L 2300/0864; B01L 2300/0867; B01L 2300/087; B01L 2300/0874; B01L 2300/0893; B01L 2300/0896; G01N 1/40; G01N 1/4005; Y10S 977/70; Y10S 977/701; Y10S 977/707; Y10S 977/712
    USPC .............. 210/459, 483, 488, 500.21, 500.22, 210/500.23, 500.25, 321.6, 321.77, 321.8, 210/321.84, 321.86, 321.89; 216/2; 422/502, 503, 507, 534; 435/297.1, 435/297.2, 297.4, 308
    See application file for complete search history.

(56) References Cited

U.S. PATENT DOCUMENTS

| | | | |
|---|---|---|---|
| 5,798,042 A * | 8/1998 | Chu | A61K 9/0024 |
| | | | 210/490 |
| 5,938,923 A * | 8/1999 | Tu | B01D 39/2072 |
| | | | 210/490 |
| 6,228,744 B1 | 5/2001 | Levine et al. | |
| 6,962,823 B2 * | 11/2005 | Empedocles | B81C 99/008 |
| | | | 438/105 |
| 2002/0125192 A1 * | 9/2002 | Lopez | B01L 3/502746 |
| | | | 210/656 |
| 2004/0099946 A1 | 5/2004 | Dickey et al. | |
| 2005/0215025 A1 | 9/2005 | Chang et al. | |
| 2006/0040375 A1 * | 2/2006 | Arney | B01L 3/508 |
| | | | 435/287.1 |
| 2009/0274580 A1 * | 11/2009 | Kornblit | B01F 5/0619 |
| | | | 422/400 |
| 2012/0125848 A1 * | 5/2012 | Friedberger | B01D 67/0062 |
| | | | 210/650 |
| 2012/0126449 A1 | 5/2012 | Hart et al. | |
| 2014/0021133 A1 * | 1/2014 | Siwy | B01D 67/0062 |
| | | | 210/650 |
| 2014/0224658 A1 * | 8/2014 | Richardson | B01D 46/40 |
| | | | 204/630 |
| 2015/0283512 A1 * | 10/2015 | Song | B01D 61/425 |
| | | | 210/490 |
| 2016/0059234 A1 * | 3/2016 | Chang | B01L 3/502753 |
| | | | 435/309.1 |
| 2016/0067634 A1 * | 3/2016 | Richardson | B01L 9/527 |
| | | | 210/488 |
| 2017/0008781 A1 * | 1/2017 | Richardson | C02F 1/48 |

\* cited by examiner

METHOD OF FORMING MICRO-PIPES ON A SUBSTRATE AND A STRUCTURE FORMED THEREOF

CROSS-REFERENCE TO RELATED APPLICATIONS

The present application is a non-provisional patent application claiming priority to European Patent Application No. EP 16183687.9, filed on Aug. 11, 2016, the contents of which are hereby incorporated by reference.

FIELD OF THE DISCLOSURE

The present disclosure is related to the field of semiconductor manufacturing. More specifically, the present disclosure relates to the field of producing structures comprising single or multiple layers of micro-pipes in the substrate.

BACKGROUND

Micro-pipes can offer solutions for a variety of industries for a variety of applications. It is important to control the size of the micro-pipes as well as the feasibility of the method to produce them suited for their function.

One of the conventional methods of forming micro-pipes is disclosed in U.S. Pat. No. 6,228,744 B1. In this disclosure, a micro-pipe is formed by forming a second layer over a first layer, on a substrate having a trench with a height larger than a width thereof, so that the second layer lines sidewalls and bottom of the trench and covers the top of trench to form the micro-pipe within the trench. A drawback inherent to this disclosed method is that it is unsuitable for producing micro-pipes within a trench having a width less than 100 nm, since the filling characteristics of the trench by the second layer may be limited for the formation of micro-pipes.

Another conventional method of fabricating a micro-pipe is disclosed in US 2005/0215025 A1. In this disclosure, a trench is provided in a base layer on a substrate. A photoresist layer on the base layer covers the trench. Subjecting the photoresist layer to ionizing radiation forms a micro-pipe. A drawback inherent to this disclosed method is that the radius of curvature of the deformed photoresist portions may be dependent on a variety of factors including the photoresist material type, the thickness of the photoresist layer, the width and depth of the patterned openings, the wavelength and intensity of irradiation and the ambient pressure. Furthermore, the disclosed method is suited for producing large micro pipes, where by a photoresist layer having a thickness of about 1 um to about 100 um is provided.

Therefore, there is a need in the art for producing structures comprising single or multiple layers of micro-pipes having a cross section taken perpendicularly to their longitudinal direction having a maximal extent less than 100 nm.

SUMMARY

The present disclosure provides methods to allow producing structures comprising micro-pipes.

Some embodiments of the present disclosure allow for an improved way of producing structures comprising micro-pipes.

Some embodiments of the present disclosure allow for producing structures comprising micro-pipes having a cross section taken perpendicularly to their longitudinal direction having a maximal extent less than 100 nm.

Some embodiments of the present disclosure allow for producing structures comprising micro-pipes is compatible with semiconductor fabrication.

Some embodiments of the present disclosure allow for producing structures comprising multiple layers of micro-pipes.

Some embodiments of the present disclosure allow for producing structures comprising micro-pipes suitable for use in semiconductor industry such as for the purpose of cooling semiconductor devices, or in biotechnological, chemical, biological, bio-chemical, micro-biological or molecular-biological industries such as for filtering or for fluid control purposes or in other industries, where single layer or multiple layers of micro-pipes are demanded.

In a first aspect, the present disclosure relates to a method for producing a structure comprising, on a main surface of a substrate, at least one elongated cavity having openings at opposing ends. The method comprises providing a substrate having a main surface. A first pair of features are formed on the main surface. The features protrude perpendicularly from the main surface. The features have elongated sidewalls and a top surface and are parallel to one another. They are separated by a gap having a width B1 and a bottom surface. The features have a width of w and a height h. The ratio of h/w is in the range of 3 to 30 and the separation gap $s_1$ is less than twice the height h and the width w is in the range between 100 nm and 5 nm. At least the main surface of the substrate and the first pair of features are brought in contact with a liquid. This liquid is suitable for making a contact angle of less than 90° with the material of the elongated sidewalls. Subsequent to the rinsing, the substrate and the first pair of features are dried, thereby causing an upper part of the features to contact each other forming the at least one elongated cavity.

The embodiments disclosed herein describe a method of forming elongated cavities or in other words, micro-pipes, using semiconductor manufacturing. This is achieved by causing the upper part of the features contact each other, thereby leading to the upper parts to stick or in other words to join together. This is achieved by bringing this substrate in contact with a liquid that is susceptible of or suitable for making a contact angle of less than 90° with the material of the elongated sidewalls.

The present disclosure also takes advantage of the fact that micro-pipes having a cross section taken perpendicularly to their longitudinal direction having a maximal extent less than 100 nm can be produced. This is achievable due to the fact that the gap width $s_1$ separating the features in a pair or the gap $s_2$ between neighboring pairs may be tuned as desired thanks to the fact that this method can be carried out by semiconductor manufacturing.

In some embodiments, the at least one elongated cavity may have openings only at opposing ends, where the opposing ends are oriented in the longitudinal direction of the at least one elongated cavity.

In some embodiments, the at least one elongated cavity may be an elongated enclosed cavity.

In some embodiments, the features of the first pair may be identical features.

In some embodiments, forming, on the main surface, the first pair may further comprise forming at least a second pair identical to the first pair. This at least second pair may be separated from the first pair by a gap having a width $s_2$ higher or equal to $s_1$.

In some embodiments, the gap having the width $s_1$ may be smaller than 100 nm. This allows for producing micro-pipes, for which a cross section taken perpendicularly to their longitudinal direction having a maximal extent less than 100 nm can be produced.

In some embodiments, s1 may be in the range between 100 nm and 5 nm.

The at least second pair may be separated from the first pair by a gap having a width s2 higher than s1 since this allows stiction (or joining or contacting of the upper parts of the features) to occur in a more controlled way.

The at least second pair may be separated from the first pair by a gap having a width "s2" equal to "s1" since this allows stiction (or joining or contacting of the upper parts of the features) and allows for forming elongated cavities having equal size and spacing. Having equal size and spacing corresponds to pattern density being equal to unity.

In some embodiments, the width w is in the range between 100 nm and 5 nm, which improves the ability to obtain stiction of the upper parts of the features. Besides, it leads to obtain small and uniform micro-pipes since the width of the features will correspond to the wall thickness of the micro-pipes formed due to stiction.

In some embodiments, the features and the bottom area may be made of the same material. This way the inner surface of the elongated cavities will be of the same material.

In some embodiments, the structure comprising such elongated cavities may be used for filtering purposes, for example filtering of a single component from a fluid, wherein the fluid may be a liquid mixture or a gas mixture.

In some embodiments, the features and the bottom area may be made of different materials.

In some embodiments, the structure comprising such elongated cavities may be used for filtering purposes, for example filtering of two different components from a fluid, wherein the fluid may be a gas mixture or a liquid mixture. While one component may show affinity for inner sidewalls and inner top surface, another component may show affinity for the bottom area, which actually forms the bottom area of each of the elongated cavities.

In some embodiments, the method may further comprise, after forming the first pair on the substrate, providing a conformal layer on the substrate and the first pair.

In some embodiments, the conformal layer allows for covering the main surface of the substrate following its topography and the topography of the first pair. This allows for producing a variety of structures comprising elongated cavities having different inner surfaces. Thus, the structure may be produced suited for a specific purpose as a function of the type of the material of the conformal layer chosen. This allows for obtaining structures with elongated cavities having inner surfaces that may be formed of a different material than the material forming the substrate and/or the features. Different conformal layers may be provided on different parts of the substrate by using masking techniques thus, increasing the functionality of the structure. This then opens up the window for having more possibilities of use of a single structure comprising different elongated cavities tuned, for example, for filtering of multiple components from a fluid, wherein the fluid may be a gas mixture or a liquid mixture.

In some embodiments, the method may further comprise, after providing the conformal layer, performing an anisotropic etching process. Anisotropic etch process removes the conformal layer from the top surfaces of the features and from the main surface.

This allows for having elongated cavities where a bottom portion of their inner surface is different than the rest of the inner surface. In this way, selective adsorption of a desired molecule can be achieved, which may be for the purpose of filtering. This may be useful in chemical, biological, biochemical, micro-biological or molecular-biological applications.

Furthermore, one can make use of the difference in reflectivity between the material of the bottom area and the rest of the inner surface of such elongated cavities for suited applications.

In some embodiments, the method may further comprise, before bringing at least the main surface of the substrate, and the first pair of features, in contact with the liquid, making the features hydrophilic.

Making the features hydrophilic is advantageous since it makes it possible to use a variety of materials for forming the pair of features, whereby, in some embodiments, the liquid may include water.

In some embodiments, the liquid may consist only of water. This is advantageous since water is typically available in most manufacturing facilities, including in semiconductor manufacturing facilities.

In some embodiments, the liquid may consist only of de-ionized water.

In some embodiments, the method may further comprise after drying, providing, overlying the substrate and the at least one elongated cavity formed, a first layer having a planar top surface parallel to the main surface. On the planar top surface, a third pair of features being as described for the first pair of features may be formed. The third pair may protrude from the planar top surface. At least the planar top surface and the third pair may be brought in contact with a liquid, after which it may be subsequently dried Layers of elongated cavities stacked on top of each other may be obtained on the same substrate. Depending on the purpose and type of the application, such a substrate comprising stacked elongated cavities may allow for improved throughput and efficiency.

In some embodiments, elongated cavities in each layer in the stack may be aligned, anti-aligned or positioned at an angle of θ (theta), which is 90°<θ<180°, with respect to the elongated cavities of the layer above or below.

In some embodiments, bringing the substrate in contact with the liquid may be carried out in a recipient such as for example a tank filled with the liquid or a spray tool, whereby the liquid is sprayed on to the main surface of the substrate.

In a second aspect, the present disclosure relates to a structure comprising a substrate having a main surface and at least one elongated cavity on the main surface. The at least one elongated cavity has openings at opposite ends and a bottom area and it is confined by a first pair of features. The features protrude, at a lower part, perpendicularly from the main surface at a separation width of s1 from each other and are contacted to each other at an upper part opposite to the lower part. The separation width decreases in a direction from the lower part to the upper part. The features have elongated sidewalls and a width w, wherein the width w is in the range between 100 nm and 5 nm.

In some embodiments, the contacted upper parts of the features may be dome-shaped or triangular roof-shaped.

In some embodiments, s1 may be in the range between 100 nm and 5 nm.

This range may be beneficial where micro-pipes of cross section taken perpendicularly to their longitudinal direction having a maximal extent less than 100 nm is desired can be produced.

In some embodiments, the at least one elongated cavity may be separated from a neighboring identical elongated cavity by a gap s2 having a width higher or equal to s1.

The elongated cavity and the neighboring elongated cavity are separated from each other by a gap s2 having a width equal to s1, which allows for a structure having uniformly distributed elongated gaps over a certain surface area such that the pattern density becomes close to unity. This structure is beneficial when used in applications where having pattern density close to unity plays an important role.

The elongated cavity and the neighboring elongated cavity are separated from each other by a gap s2 having a width higher than s1, which allows for a structure comprising elongated gaps having a pattern density less than unity. In this way, on different regions of the surface of a structure, micro-pipes having pattern densities different than unity can be produced.

In some embodiments, the features and the bottom area may be made of different material. This is beneficial in applications where the structure comprising such elongated cavities may be used for filtering purposes, for example filtering of two different components from a fluid, where the fluid is a gas mixture or liquid mixture. While one component may show affinity for inner sidewalls and inner top surface, another component may show affinity to the bounded part of the main surface, which forms the bottom area of each of the elongated cavities.

In some embodiments, the inner surfaces of the at least one elongated cavity may be covered with a layer. This allows for structures comprising elongated cavities having inner surfaces covered with the layer, whereby the structures may be suited for a specific purpose as a function of the type of the material of the layer.

In some embodiments, the structure may further comprise at least one connector for connecting one of the openings of the at least one elongated cavity to a fluid supply.

In some embodiments, the fluid supply may be adapted for supplying a liquid mixture or a gas mixture.

In a third aspect, the present disclosure relates to a filtering device comprising the structure of the second aspect.

Some embodiments of the present disclosure allow for the filtering device to be used for filtering purposes where only a small amount of fluid is sufficient thanks to the size and density of the elongated cavities comprised in the structure. This filtering device may be used in biotechnological, chemical, biological, bio-chemical, micro-biological or molecular-biological industries.

Some aspects of the disclosure are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices and methods in this field, the present concepts are believed to represent substantial new and novel improvements, including departures from prior practices, resulting in the provision of more efficient, stable and reliable devices or methods of this nature.

The above and other characteristics the present disclosure will become apparent from the following detailed description, taken in conjunction with the accompanying drawings, which illustrate, by way of example, the principles of the disclosure. This description is given for the sake of example only, without limiting the scope of the disclosure. The reference figures quoted below refer to the attached drawings.

BRIEF DESCRIPTION OF THE FIGURES

The above, as well as additional, features will be better understood through the following illustrative and non-limiting detailed description of example embodiments, with reference to the appended drawings.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof.

Reference throughout the specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout the specification are not necessarily all referring to the same embodiment, but may. Furthermore, the particular features, structures or characteristics may be combined in any suitable manner, as would be apparent to one of ordinary skill in the art from the disclosure, in one or more embodiments.

Similarly it should be appreciated that in the description of some embodiments of the disclosure, various features are sometimes grouped together in a single embodiment, figure, or description thereof for the purpose of streamlining the disclosure and aiding in the understanding of one or more of the various aspects. The method of disclosure, however, is not to be interpreted as reflecting an intention that the disclosure requires more features than are expressly recited in each claim. Rather, as the following claims reflect, aspects lie in less than all features of a single foregoing disclosed embodiment. Thus, the claims following the detailed description are hereby expressly incorporated into the detailed description, with each claim standing on its own as a separate embodiment of the disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that some embodiments may be practiced without these specific details. In other instances, well-known methods, structures and techniques have not been shown in detail in order not to obscure an understanding of the description.

The following terms are provided solely to aid in the understanding of the disclosure.

As used herein and unless provided otherwise, elongated cavity and micro-pipes may be used interchangeably.

As used herein and unless provided otherwise, "rinsing" refers to removal of contaminants or etch by-products using liquids.

As used herein and unless provided otherwise, "rinsing liquid" refers to the liquid, liquids or mixture of liquids used in the rinsing process.

As used herein and unless provided otherwise, "stiction" refers to the phenomenon where a part of the features are joined or contacted together. The joined or contacted parts may refer to an upper part opposite to a lower part, from which the features protrude perpendicularly from the main surface.

As used herein and unless provided otherwise, "exposed" refers to structures or features being in contact with the ambient.

As used herein and unless provided otherwise, "pattern density" refers to, within a defined region having a certain total surface area, the ratio of the surface area covered by a structure or structures to the surface area not covered by the structure or structures.

As used herein and unless provided otherwise, "identical" refers to the features or elongated cavities having a difference of less than 5% in any of their physical dimensions, such as the width, the height, and/or the length, with respect to one another.

As used herein and unless provided otherwise, "elongated sidewalls" refer to the physical dimension of the features in the third dimension, which may be characterized by referring their length.

As used herein and unless provided otherwise, "dome-shaped" refers to being shaped like a hemi-sphere.

As used herein and unless provided otherwise, "triangular roof-shaped" refers to being shaped like a triangle.

Figure 1:
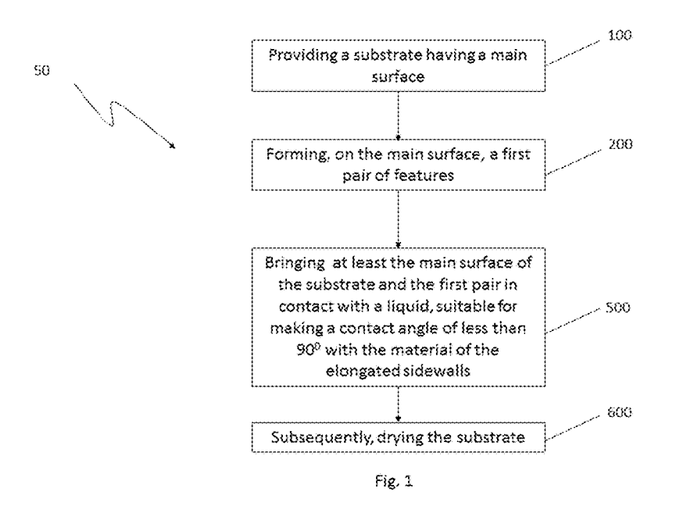
FIG. 1 shows a flowchart representing a method, according to an example embodiment.

We now refer to FIG. 1 showing a flowchart representing a method according to an embodiment of the present disclosure and FIG. 2a to FIG. 2f showing schematically alternatives of a substrate (10), where the first pair of features (45) separated by a gap (41) having the width s1, according to embodiments of the present disclosure, are formed on its main surface. The features protrude at a lower part (1) perpendicularly from the main surface (30) and are free at an upper part (2) opposite to the lower part (1). s1 refers to the width of the gap between the features (45) measured typically in between the opposite elongated sidewalls of the features of a pair that face each other and at the lower part (1) where they protrude perpendicularly from the main surface (30).

The method (50) starts with providing (100) a substrate (10) having a main surface (30).

In some embodiments, the substrate may be any underlying material or materials that may be used, or upon which a device may be formed.

In some embodiments, the substrate (10) may comprise a dielectric layer.

In some embodiments, the substrate (10) may be a dielectric substrate.

In some embodiments, the substrate (10) may be a metal substrate.

In some embodiments, the substrate (10) may comprise a metal layer.

A first pair of features (45) is formed (200) on the main surface (30). The features (45) protrude perpendicularly from the main surface (30) and extend away from the main surface. They have elongated sidewalls (40) and a top surface (70). They are parallel to one another and the elongated sidewalls on opposing sides of each of the features face each other. They are separated by a gap (41) having a width s1 and a bottom area such that they bound a part of the main surface (30) in between them. They have a width w1 and a height h. The ratio of h/w is in the range of 3 to 30 and the separation gap s1 is less than twice the height h1". The width w of the features is in the range between 100 n and 5 nm. The width of the features may be chosen according to the application to which the micro-pipes will serve. For example, for nano-fluidic applications, normally the wall of the micro-pipe(s) is rigid and thick, otherwise the capillary pressure can easily deform and close micro-pipe. Thus, for such applications, the width is in the range between 100 nm and 50 nm. For applications where liquid or bio-molecules with resolution on the nanometer scale is desired, micro-pipes having a wall thickness in the range between 50 nm and 5 nm is desired so that electron beam can transmit through.

In some embodiments, the features may be identical to one another such that their physical dimensions, such as the width, the height and the length, may be different at most up to 5% with respect to one another.

In some embodiments, there may be an insulator layer (20) on the main surface (30) of the substrate (10) as shown in FIG. 2a and FIG. 2b.

In some embodiments, the substrate (10) may be a semiconductor substrate suitable for manufacturing semiconductor devices, such as Group IV element, for example, silicon, germanium, silicon germanium or a compound semiconductor such as Group III-V.

The substrate may also be silicon-on-glass, silicon-on sapphire, silicon-on-insulator (SOI) substrate or germanium-on-insulator (GeOI) substrate. The first pair of features (45) protrude from the main surface (30) of the substrate (10). The pair of features (45) may be formed in a recess in the insulator layer (20). The pair of features (45) may thus have a buried portion (45") within the recess and an upper portion (45') on the buried portion protruding from the main surface (30). This insulating layer (20) may be a silicon oxide or silicon nitride. Typically, this silicon oxide is silicon dioxide and insulating layer features in between the pair of features are called shallow trench isolation (STI) features. Thus, shallow trench isolation-first (STI-first) approach may be used to form the pair. Shallow trench isolation-last (STI-last) approach may also be used to form the pair.

Figure 2:
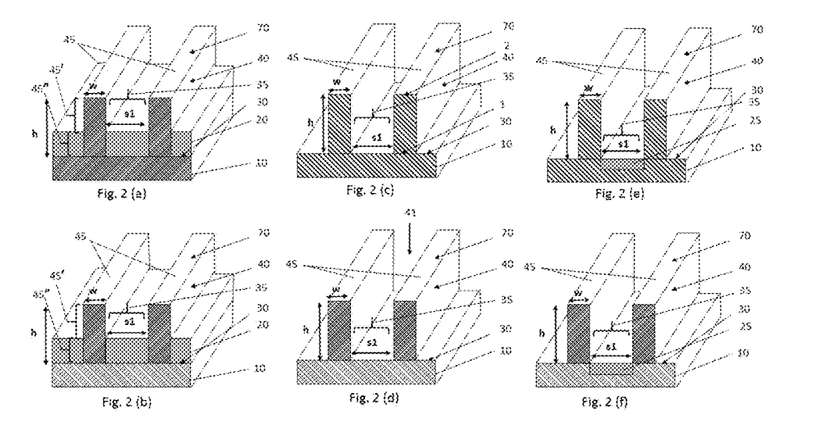
FIG. 2a to FIG. 2f show schematically alternatives of substrates comprising a first pair of features separated by a gap "s1," according to an example embodiment.

The pair of features (45) and the substrate (10) may be of the same material as in FIG. 2a or from different materials as in FIG. 2 b. In some embodiments, pair of features (45) and/or the semiconductor substrate (10) may comprise different semiconductor layers stacked on top of one another, such as for example silicon germanium (SiGe) vs. germanium (Ge) or silicon (Si) vs. silicon germanium (SiGe).

In alternative embodiments, the substrate (10) may be a bulk semiconductor substrate (as shown in FIG. 2c to FIG. 2f) such as for example, Si, Ge, gallium arsenide (GaAs), a gallium arsenide phosphide (GaAsP), an indium phosphide (InP) or a silicon germanium (SiGe) substrate or it may comprise different semiconductor layers stacked on top of one another, such as for example silicon germanium (SiGe) vs. germanium (Ge) or silicon (Si) vs. silicon germanium (SiGe).

The substrate (10) may also be a dielectric material such as for example silicon nitride.

In these alternative embodiments, the first pair of features (45) and the substrate (10) from which they protrude may be made of the same material, for example from the same semiconductor or the same dielectric material, as shown in FIG. 2c and FIG. 2e. The substrate (10) and the pair of features (45) may for example be silicon nitride. Formation of features such as shown in FIG. 2c to FIG. 2f may be done by using Self Aligned Multiple Patterning (SAMP) Techniques, such as for example self-aligned double patterning (SADP) or self-aligned quadrupole patterning (SAQP). In SAMP techniques, a core layer, typically provided on a hard mask layer, is patterned, followed by a conformal coverage of the patterned core layer, by a dielectric layer, which is typically a silicon nitride or a silicon oxide. Following anisotropic etching, whereby the dielectric layer is removed from the horizontal surfaces, and subsequently performing removal of the core patterns, features (45) may be obtained. Thus, the spacing s1 may be adjusted by the critical dimension (CD) or in other words, by the width of the core patterns. Trimming of the core patterns may be an option to reduce the CD, thus to reduce the spacing value s1. Furthermore, the separation between the core patterns, which is dictated by the mask design, then determines the value s2, which, eventually, refers to the gap between neighboring pairs.

Yet, in these alternative embodiments, the first pair of features (45) and the substrate (10) from which they protrude may be made of a different material, for example from different semiconductor materials and/or different dielectric materials, as shown in FIG. 2d and FIG. 2f.

In some embodiments, the features (45) and the bottom area of the gap in between the features (45) may be made of the same material, as shown in FIG. 2c.

In alternative embodiments, the features (45) and the bottom area of the gap in between the features (45) may be made of different material, as shown in FIG. 2a, FIG. 2b, FIG. 2d, FIG. 2e and FIG. 2f.

The fact that the pair of features (45) and the bottom area of the gap in between the features may be made of the same material or a different material may be beneficial depending on the type of application the micro-pipes are intended to be used for, such as for example for filtering applications where filtering of a single component or two components may be desired.

Returning back to FIG. 1, at least the main surface of the substrate (10) and the first pair of features (45) are brought into contact (500) with a liquid. The liquid is suitable for making a contact angle of less than 90° with the material of the elongated sidewalls (40). Subsequently, the substrate (10) is dried (600), thereby causing an upper part of the features (45) to contact or join each other thereby forming the at least one elongated cavity (11). The upper part of the features are contacted to each other along the length of the features and thus, leads to the formation of openings at opposing ends of the at least one elongated cavity formed. The opposing ends are oriented in the longitudinal direction of the at least one elongated cavity.

Contact angle that the liquid makes with the material of the elongated sidewalls can be measured by typical contact angle measurement techniques. Measurement of contact angle may be carried out by using an optical tensiometer or a force tensiometer. A substrate overlaid homogeneously by the material of the elongated sidewalls on one side or on both sides and the liquid of interest can be used for contact angle measurement. The liquid resulting in a contact angle of less than 90° on the material of the elongated sidewalls is suitable according to embodiments of the present disclosure.

In some embodiments, the substrate (10) may be dried alone or together with other substrates. Drying may be performed by drying processes, such as for example, spin drying, air/$N_2$ flow drying, isopropyl alcohol (IPA) drying, evaporation drying, or drying by heating the substrate.

Figure 3:
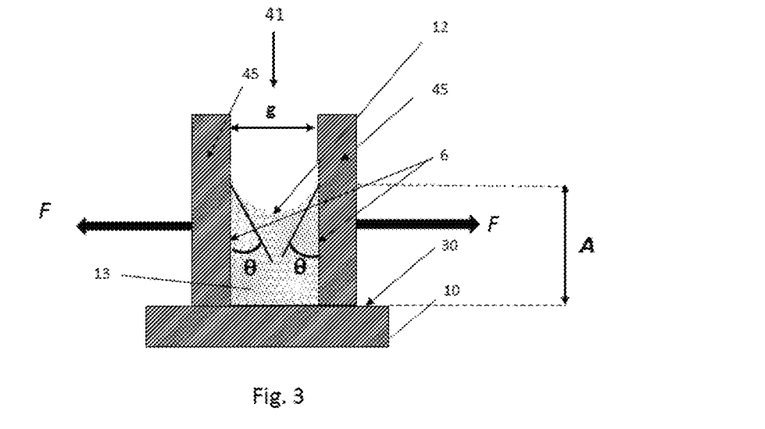
FIG. 3 shows the forces acting on features that result in stiction, according to an example embodiment.

We now refer to FIG. 3. Stiction problem originates from capillary forces when there is a thin layer of liquid between the surfaces of two features that face each other such that the thin layer of liquid can work as an adhesive. If the contact angle between the liquid and the surface is less than 90°, the pressure inside the liquid drop will be lower than outside and a net attractive force exists between the features. The pressure difference $\Delta pla$ at the liquid-air interface is given by the Laplace equation:

$$\Delta pla = \gamma\_la/r \qquad \text{(Eq. 1)}$$

where $\gamma\_la$ is the surface tension of the rinsing liquid-air interface, and r is the radius of the curvature of the meniscus (12). The liquid (13) is between the features (45) and the liquid (13) contacts the elongated sidewalls on opposing sides (6) of each of the features (45) that face each other at a fixed contact angle (θ). From geometry it follows that;

$$r = -g/2 \cos \theta \quad \text{(Eq. 2)}$$

In equilibrium, an external force (F) separating the features (45) counterbalances the capillary pressure forces such that;

$$F = \Delta p l a A = (2 A \gamma\_la \cos \theta)/g \quad \text{(Eq. 3)}$$

where A is the wetted area. A positive value for F corresponds to a negative Laplace pressure. The pressure inside the liquid (13) is lower than outside and the features (45) are pushed together by pressure forces, thus causing stiction.

Figure 4:
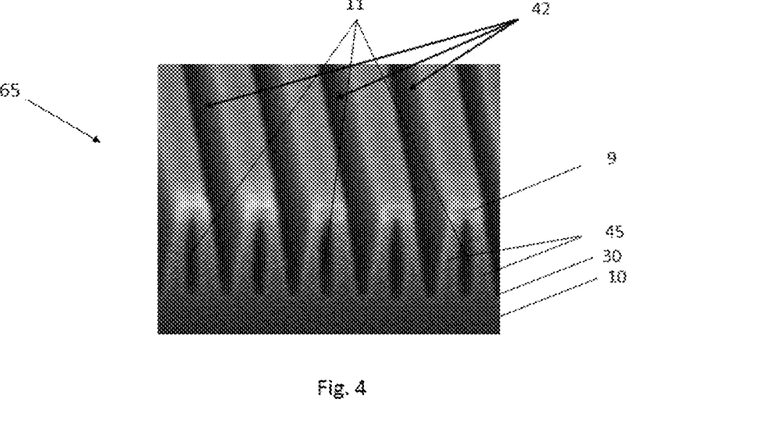
FIG. 4 shows a tilted Cross Section Scanning Electron Microscopy (X-SEM) image of micro-pipes comprised on a main surface of a substrate, according to an example embodiment.

FIG. 4 shows a tilted cross section Scanning Electron Microscopy (SEM) image of a structure (65) comprising a substrate (10) having a main surface (30). The substrate is a semiconductor material. This semiconductor material (10) is bulk silicon. Upper parts of features (45) patterned in the bulk silicon substrate (10) are contacted to each other after bringing the substrate in contact with the liquid comprising water, which is subsequently dried. The features (45) still possess the patterned hard mask (25) on their upper portion, which is typically deposited as a layer overlying the silicon substrate (20) before patterning in order to facilitate the etching process. As a result of joining of the upper parts of the features (45), elongated cavities (11) are produced on the main surface (30) running parallel to each other with openings at opposing ends.

Figures 5A, 5B:
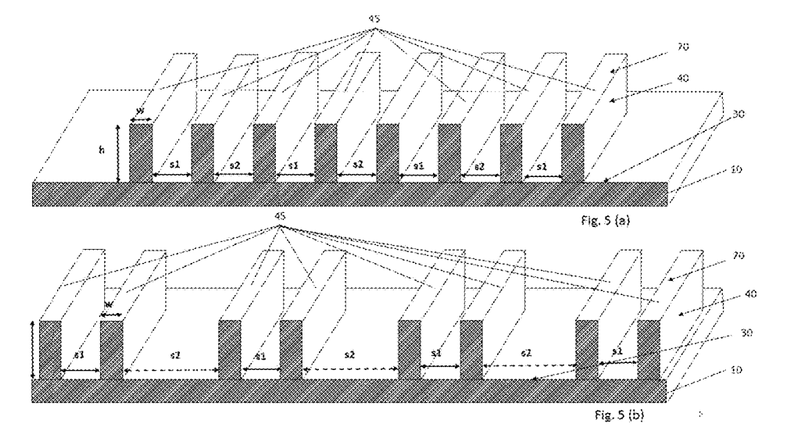
FIG. 5a and FIG. 5b show schematically pairs of features separated from each other by a gap having a width "s2" (a) equal to "s1" and (b) higher than "s1," according to an example embodiment.

FIG. 5a and FIG. 5b show schematically pairs of features (45), on the substrate (10), and the features (45) may be made of the same material. The features (45) of each pair is separated from each other by a gap (41) having a width s1.

In some embodiments, the width s1 between the features (45) of each pair may be equal to the separation width between consecutive pairs present on the main surface (30) of the substrate (10) as shown in FIG. 5a. This allows for obtaining elongated cavities (11) having size or, in other words, width equal to the spacing between them.

In alternative embodiments, the width s1 between the features (45) of each pair may be smaller than the separation width s2 between consecutive pairs present on the main surface (30) of the substrate (10) as shown in FIG. 5b. Having a separation distance s2 between neighboring pairs higher than that of s1 in between the features (45) allows elongated cavities (11) to be formed in a more controlled way. Furthermore, it helps to create elongated cavities (11) with a certain pattern density. Thus, by adjusting the value of s1 and s2, a desired pattern density within a certain area of the substrate may be obtained.

In some embodiments, s1 may be less than 100 nm.

In some embodiments, s1 may be in the range of 100 nm to 5 nm.

The value for s2, in theory, may be a very high value, such as for example infinity, in which case it could infer that only one pair of features is present. Thus, the following would hold;

$$0 \leq s1/s2 \leq 1$$

on condition that 5 nm < s1 < 100 nm and s1 ≤ s2 ≤ ∞

It will be appreciated that the aspect ratio (A/R) of the features (45), which is given by the ratio of h1 to w1 (h1/w1), may be dependent on a variety of factors in order for the upper parts of the features to join or not. These factors include the spacing gap, s1 between the features of a pair, or in the case of plurality of pairs then the ratio of the spacing gap s1 to s2, Young's modulus of the material of the features, width of the features, surface tension of the liquid-air interface and the contact angle. Empirically, as long as w is less than 100 nm, aspect ratio in the range of 3 to 30 will, typically, allow for materials to have stiction as described in the present disclosure. A person skilled in the art can, thus, determine a suitable value for aspect ratio within that range.

By taking into consideration linear elastic beam bending and the fact that the force acting on the features is a uniformly distributed force, i.e. the capillary force, the following equation is derived with respect to aspect ratio (A/R):

$$(A/R)^4 = (h/w)^4 \leq (c E s\_1^2)/6\gamma \cos \theta w \quad \text{(Eq. 4)}$$

$$c = 1/(1+(s1/s2)^2 + 2(1-s1/s2) \\ \sqrt{\phantom{-}}(1+(s1/s2)+(s1/s2)^2 + \ldots)) \quad \text{(Eq. 5)}$$

where the constant c shows the relation between the spacing gap s1 and s2. Calculation of Eq. 4 assumes absence of geometry fluctuations that may result from processing. Furthermore, uniform width, i.e. critical dimension (CD), is assumed for the features. Additionally, positive or negative loading effects are assumed to be absent. Positive and negative loading effects are recognized by persons skilled in the art and may be referred to as the parts of the main surface having widths s1 or s2 not being at the same level with respect to each other.

Figure 6:
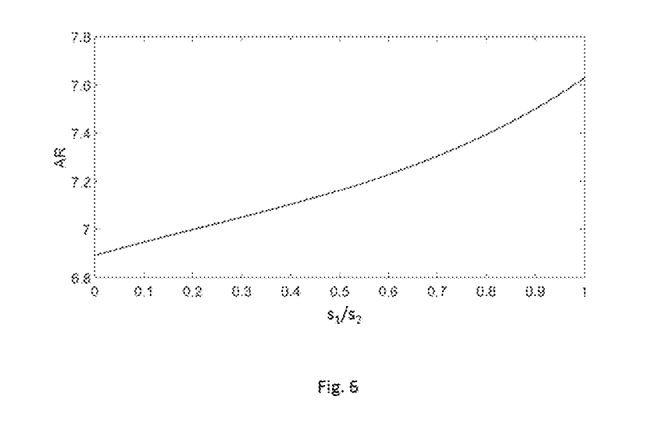
FIG. 6 shows a graph of aspect Ratio (A/R) versus ratio of spacing "s1" to "s2," according to an example embodiment.

FIG. 6 refers to the result of a simulation done by using Eq. 4 and Eq. 5, showing the change in aspect ratio versus the ratio of spacing gap s1 to s2. The features are taken to be made of silicon and the liquid is assumed to be water. Young's modulus, surface tension, s1, w and contact angle are taken as 130 GPa, 0.072 N/m, 15 nm, 10 nm and zero degrees, respectively. As the ratio of s1/s2 increases and approaches unity, the value for aspect ratio shows an increase. The curvature indicates the border line above which referred to as "region of stiction", and below which is referred to as "region of non-stiction". Thus, for example for an s1/s2 ratio of 0.5, stiction will occur for an aspect ratio value of 7.1 or above, while no stiction will occur for aspect ratio values below 7.1.

This example gives a clear indication that depending on the material, from which features are made of, the width of these features and the spacing value, as well as the type of liquid and the contact angle, the minimal value for the aspect ratio may change. Having obtained the aspect ratio from the simulation, one can further determine the height of the features since aspect ratio is given by the ratio of the height h1 to the width w1.

Figure 7A:
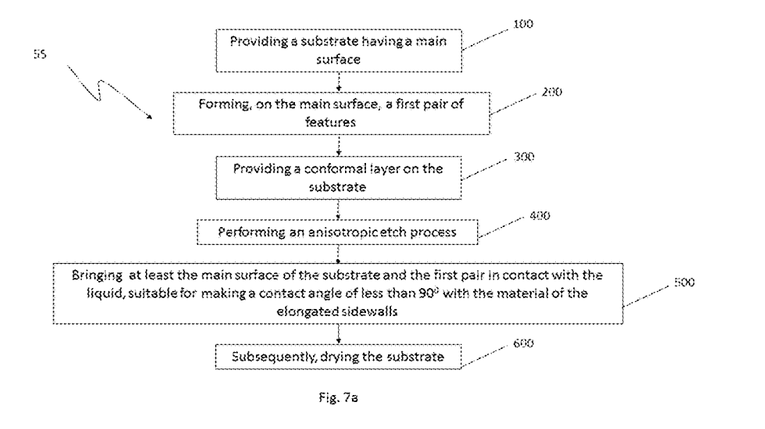
FIG. 7a shows a flowchart representing a method, according to an example embodiment.

We now return to FIG. 7, where FIG. 7a shows a flowchart representing a method according to an example embodiment.

In some embodiments, after forming (200), on the main surface (30), the first pair of features (45), a conformal layer (25) may be provided (300) on the substrate (10) and the first pair of features (45). This conformal layer (26) follows the topography of the surface. (FIG. 7b) The thickness of this conformal layer (26) may be the same on horizontal parts and on vertical parts of the main surface of the substrate (10). This may be achieved by performing an Atomic Layer Deposition process (ALD). In this case, the thickness of this conformal layer may be in the range of 0.2 nm to 20 nm. The conformal layer may also be grown epitaxially depending on the material of the features (45).

Figure 7B:
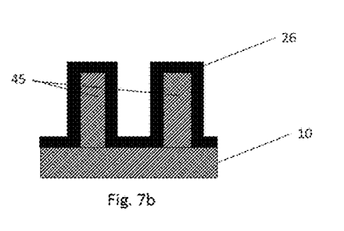
FIG. 7b show schematically features after providing a conformal layer, according to an example embodiment.

The thickness of this conformal layer (26) may be higher on horizontal parts of the main surface of the substrate than on vertical parts and this may be achieved by performing a Chemical Vapor Deposition (CVD) process or a Physical Vapor Deposition process.

The conformal layer (26) may have such properties that are suited for specific use of the micro-pipes (11), and thus, providing the conformal layer (26) allows for tuning the use of the micro-pipes. The conformal layer may be an insulating layer, a conductive layer or a semi-conductive layer.

Figure 7C:
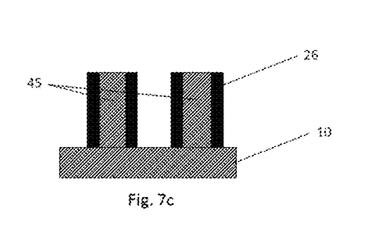
FIG. 7c show schematically features after performing anisotropic etching, according to an example embodiment.

In some embodiments, an anisotropic etch process may be performed (400) to remove the conformal layer (26) from the horizontal parts of the main surface of the substrate (10), thereby leaving the conformal layer only on vertical parts. In other words, anisotropic etching removes the conformal layer (26) from the top surfaces of the features (45) and from the main surface (30) of the substrate (10). Thus, following the anisotropic etching process, the conformal layer (26) only remains on the elongated sidewalls (40) of the features (45) as shown in FIG. 7c.

Removal of the conformal layer (26) from the horizontal parts of the substrate (10) allows, after forming the micro-pipes (11), the inner surfaces of the micro-pipes (11) to have parts with differing properties, such that the inner side walls are different than the bottom part of the elongated cavity, where the bottom area (35) of the gap (41) now actually forms the bottom part (35) of the elongated cavity (11). Thus, performing anisotropic etch process may also allow the formation of micro-pipes to be suited for specific type of applications.

In some embodiments, the features (45) may be made hydrophilic before bringing at least the main surface of the substrate (10) and the first pair of features (45) in contact with the liquid. Making the features (45) hydrophilic may be done by applying a surface treatment. This surface treatment may be a wet chemical treatment whereby a hydrophilic treatment agent may be used. The hydrophilic treatment agent may react with the exposed surfaces of the features to form a hydrophilic surface film. The surface treatment may also be a dry treatment. The dry treatment may modify the exposed surface of the features (45) forming the hydrophilic surface film. Formation of such a hydrophilic surface film may allow using a liquid comprising water, which is typically available in most manufacturing facilities, including semiconductor manufacturing. The liquid, in this case, may also only consist of water. The liquid may also be de-ionized water.

FIG. 8a to FIG. 8d show schematically the steps of a method for producing micro-pipes on a first layer (37) of a structure (65) comprising, on a main surface (30), micro-pipes (11), where the micro-pipes (11) in the first layer (37) are aligned with the micro-pipes on the main surface. The figures show corresponding cross-sections of the structure (65) at different stages. The method illustrated in FIG. 8a to FIG. 8d may be performed subsequent to the method illustrated in FIG. 1 or FIG. 7a.

Figure 8A:
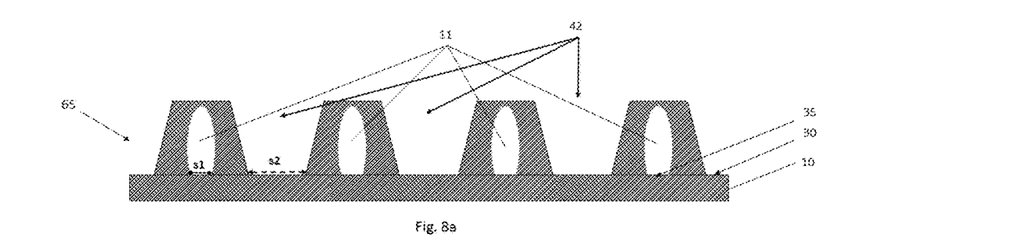
FIG. 8a to FIG. 8d show schematically the steps of a method for producing micro-pipes in a first layer on a structure comprising, on a main surface, micro-pipes, where the micro-pipes in the first layer are aligned with the micro-pipes on the main surface, according to an example embodiment.

A structure (65), as shown in FIG. 8a, is obtained according to an example embodiment. The structure (65) comprises a substrate (10) having a main surface (30) and at least one elongated cavity (11) on the main surface (30). In some embodiments, the substrate (10) may include an insulator layer. This substrate (10) may be a semiconductor material. This semiconductor material may be a bulk semiconductor, such as silicon germanium or a Group III-V compound semiconductor material or comprise layers of different semiconductor materials such silicon germanium-germanium, silicon germanium-silicon or layers of different Group III-V semiconductor materials. The at least one elongated cavity (11) has openings at opposite ends and a bottom area and is confined by a first pair of features (45). The opposing ends are oriented in the longitudinal direction of the at least one elongated cavity.

These features (45) protrude, at a lower part, perpendicularly from the main surface (30) at a separation width of s1 from each other and are contacted to each other at an upper part opposite to the lower part. The separation distance decrease in a direction from the lower part to the upper part. The features have elongated sidewalls and have a width w. The width w is in the range of 100 nm and 5 nm.

In some embodiments, the features may be identical. The identical features may be such that a difference of less than 5% in any of their physical dimensions, such as the width, the height, the length, may exist with respect to one another.

In some embodiments, the contacted upper parts of the features may be dome-shaped or triangular roof-shaped.

In some embodiments, the gap having the width s1 is smaller than 100 nm.

In some embodiments, s1 may be in the range between 100 nm and 5 nm.

In some embodiments, these features (45) and the bottom area (35) may be made of different materials, as shown in FIG. 8a, or may be made of same material.

In some embodiments, the at least one elongated cavity (11) may be separated from a neighboring identical elongated cavity by a gap (42) having a width s2. The width s2 may be higher or equal s1. This may be beneficial for the structure (65) if fluid control and movement is an important parameter associated with the relevant purposes.

Figure 8B:
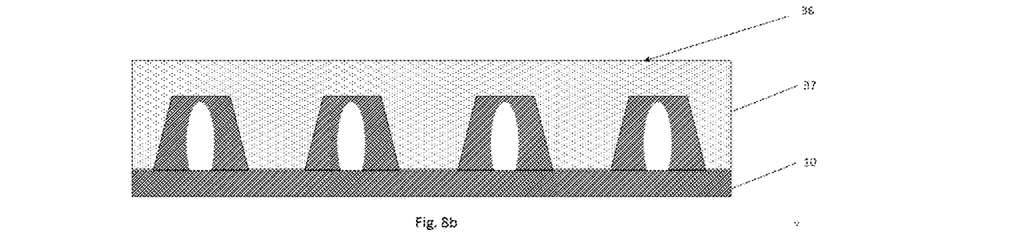

In some embodiments, after drying the substrate (10), a first layer (37) may be provided overlying the substrate (10) and the at least one elongated cavity (11) as shown in FIG. 8b. The first layer (37) may have a planar top surface (36). This planar top surface (36) may be parallel to the main surface (30).

This first layer (37) may be a self-planarizing layer, such that upon deposition on the substrate, it not only fills the spaces between the elongated cavities (11) but also forms an overburden on the top surfaces of the contacted upper parts of the elongated cavities.

This first layer (37) may also be a non-self-planarizing layer, in which case the planar top surface may be obtained by performing a planarization process subsequent to providing the first layer (37).

Figure 8C:
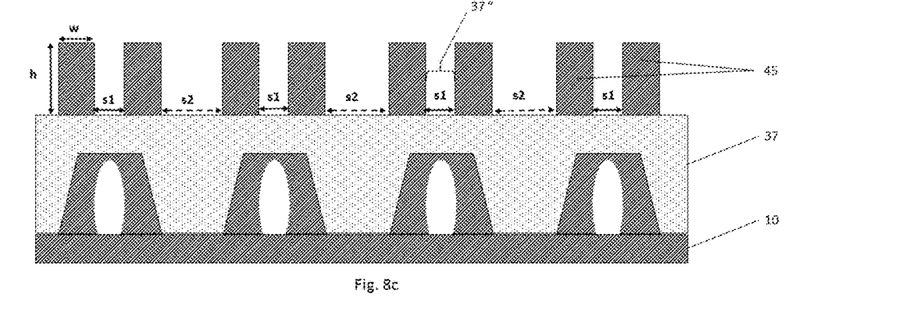

A third pair of features (45) may be formed on the planar top surface (36) (FIG. 8c). This third pair may have the same range of physical dimensions as the first pair or the third pair may be identical to the first pair. The features (45) of this third pair may have elongated sidewalls and a top surface. They may be parallel to one another and may be separated by a gap having a width s1 and a bottom area (37"). The features of this third pair may have a width w and height h and ratio of h/w may be in the range of 3 to 30. The separation gap s1 may be less than twice the height of h and the width w may be in the range between 100 nm and 5 nm. Forming the third pair of features (45) may be done by providing a second layer (not shown in the figures) on the planar top surface (36) of the first layer (37). After performing a lithographic process, whereby a photoresist layer is provided on the second layer, followed by an etching process through the second layer and stopping on the first layer (37) and subsequently removing the photoresist layer, the third pair of features (45) is formed on the first layer (37). The third pair of features may, thus, be formed from the material of the second layer. The first layer (37) and/or the second layer may be a dielectric layer. The first layer (37) may, for example, be a silicon nitride layer and the second layer may, for example, be amorphous carbon. The silicon nitride layer may be Si3N4. The second layer may also be a silicon oxide layer, whereby recesses may be formed in the silicon oxide following the lithographic and etching process. The silicon oxide layer may be SiO2. Filling the recesses with a semiconductor material that may be followed by etching back the silicon oxide and stopping on the first layer (37), leads also to the formation of the third pair. The third pair of features (45) formed on the first layer (37) may be comprised in a plurality of features (FIG. 8c). The spacing, s2, between different pairs of features on the first layer (37) may be equal to or higher than the spacing, s1, between each feature in each pair present on the first layer (37).

Figure 8D:
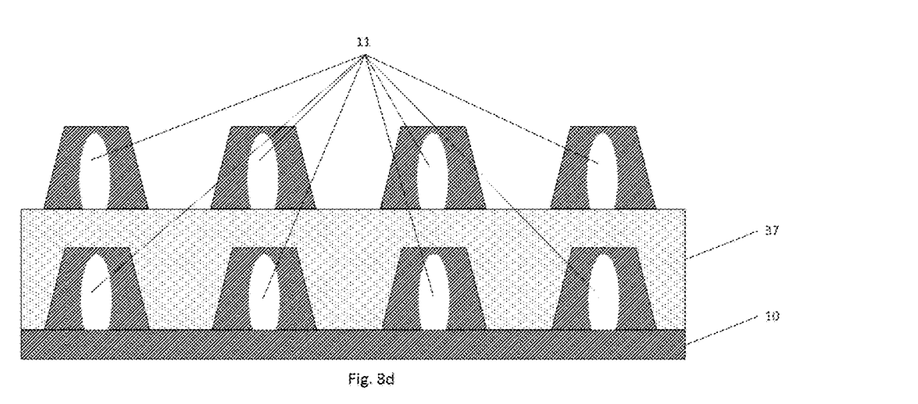

At least the planar top surface and the third pair may be brought into contact with a liquid and subsequently dried, thereby forming elongated cavity (11) on the planar top surface (36) of the first layer (37) (FIG. 8d). The liquid that is brought into contact with the planar top surface and the third pair may be the same liquid as the one that is brought into contact with at least the main surface of the substrate and the first pair of features. This liquid is suitable for making a contact angle of less than 90° with the material of the elongated sidewalls of the third pair. Further additional pairs identical to the third pair may be formed on the planar top surface (36) of the first layer (37), thus leading to the formation of further additional identical elongated cavities on the planar top surface (36) of the first layer (37). The elongated cavities (11) formed on the planar top surface (36) of the first layer (37) may be aligned with the elongated cavities (11) formed on the main surface (30) of the substrate (10).

Figure 9A:
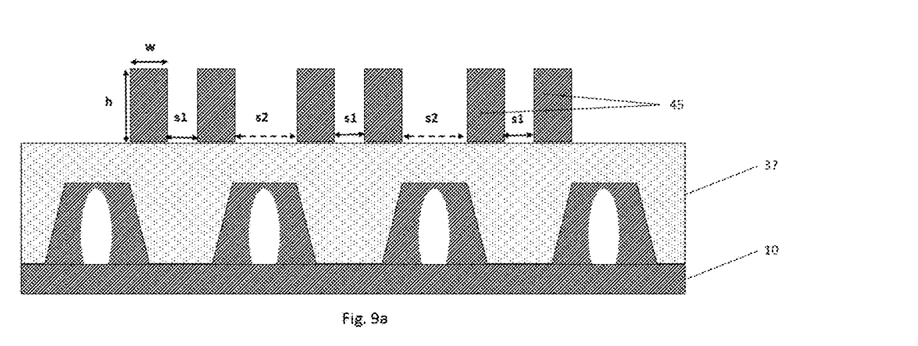
FIG. 9a and FIG. 9b show schematically the steps of a method for producing micro-pipes in a first layer on a structure comprising, on a main surface, micro-pipes, where the micro-pipes in the first layer are anti-aligned with the micro-pipes on the main surface, according to an example embodiment.
Figure 9B:
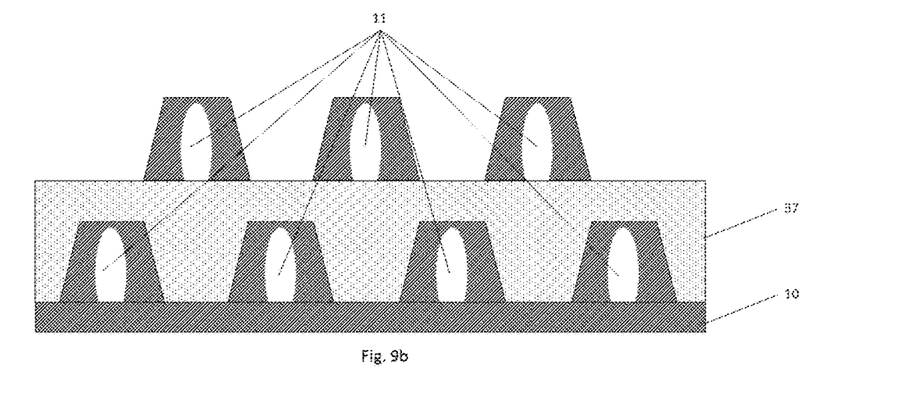

The elongated cavities formed on the planar top surface (36) of the first layer (37) may be anti-aligned with the elongated cavities (11) formed on the main surface (30) of the substrate (10) (FIG. 9b).

Having the elongated cavities (11) on the planar top surface (36) aligned or anti-aligned with those on the main surface (30) of the substrate (10) may allow for controlling the fluid dynamics and movement depending on the application in question.

Furthermore, the elongated cavities (11) formed on the planar top surface (36) of the first layer (37) may be positioned at an angle of θ (theta), which is 90°<θ<180°, with respect to the elongated cavities (11) formed on the main surface (30).

The elongated cavities formed on the planar top surface of the first layer (37) may be connected to the elongated cavities (11) formed on the main surface (30) or may be connected to other elongated cavities that may be formed on other layers overlying them.

Figure 10:
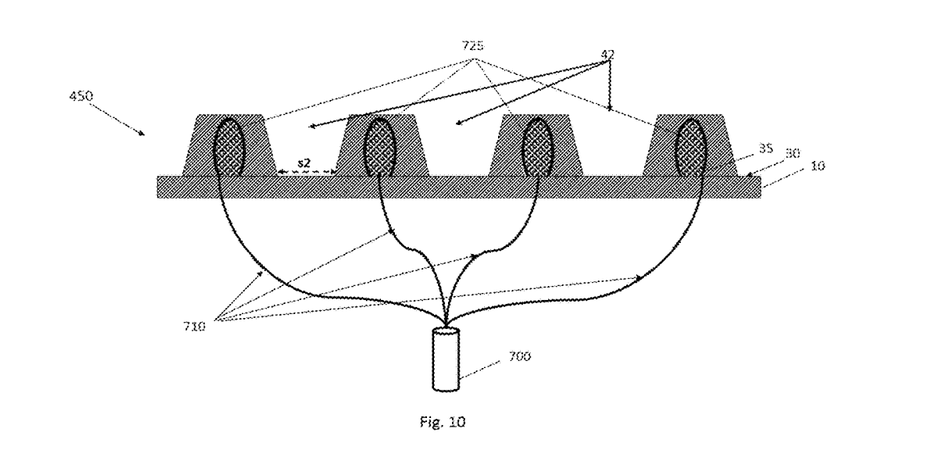
FIG. 10 shows a structure comprising at least one connector for connecting one of the openings of the at least one elongated cavity to a fluid supply, according to an example embodiment.

We now refer to FIG. 10 showing the structure (65) according to an example embodiment. In some embodiments, the structure (65) may further comprise at least one connector (710) for connecting one of the openings (725) of the at least one elongated cavity (11) to a fluid supply (700). The fluid supply may be a supply for a liquid mixture or a gas mixture.

This structure (65) is a filtering device (450) that may be used for filtering one or more liquid components or one or more gas components from a liquid mixture or a gas mixture, respectively.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. A structure comprising:
   a substrate comprising a main surface; and
   at least one elongated cavity on the main surface, wherein the at least one elongated cavity comprises openings at opposing ends and a bottom area and is confined by a first pair of features, wherein the first pair of features:
   protrude, at a lower part, perpendicularly from the main surface at a separation width of s1 from each other and are contacted to each other at an upper part opposite to the lower part, wherein the separation width decreases in a direction from the lower part to the upper part;
   comprise elongated sidewalls; and
   comprise a width w, wherein the width is within in a range between 100 nm and 5 nm.

2. The structure according to claim 1, wherein the at least one elongated cavity is separated from a neighboring identical elongated cavity by a gap s2 having a width higher or equal to s1.

3. The structure according to claim 1, wherein the first pair of features and the bottom area are made of different material.

4. The structure according to claim 1, wherein inner surfaces of the at least one elongated cavity are covered with a layer.

5. The structure according to claim 1, wherein the structure further comprises at least one connector for connecting one of the openings of the at least one elongated cavity to a fluid supply.

6. A filtering device comprising:
   a substrate comprising a main surface; and
   at least one elongated cavity on the main surface, wherein the at least one elongated cavity has openings at opposing ends and a bottom area and is confined by a first pair of features, wherein the first pair of features:
   protrude, at a lower part, perpendicularly from the main surface at a separation width of s1 from each other and are contacted to each other at an upper part opposite to the lower part, wherein the separation width decreases in a direction from the lower part to the upper part;
   comprise elongated sidewalls; and
   comprise a width w, wherein the width w is in a range between 100 nm and 5 nm.

7. The structure according to claim 1, wherein the bottom area forms a bottom part of the at least one elongated cavity.

8. The filtering device according to claim 6, wherein the bottom area forms a bottom part of the at least one elongated cavity.

* * * * *